(12) United States Patent
Forderer

(10) Patent No.: US 9,161,792 B2
(45) Date of Patent: Oct. 20, 2015

(54) SURGICAL ASSEMBLY

(71) Applicant: Stryker Trauma SA, Selzach (CH)

(72) Inventor: Aaron Forderer, Biel / Bienne (CH)

(73) Assignee: Stryker Trauma SA (CH)

( * ) Notice: Subject to any disclaimer, the term of this patent is extended or adjusted under 35 U.S.C. 154(b) by 159 days.

(21) Appl. No.: 13/895,788

(22) Filed: May 16, 2013

(65) Prior Publication Data

US 2013/0310884 A1 Nov. 21, 2013

(30) Foreign Application Priority Data

May 16, 2012 (EP) .................................... 12003869

(51) Int. Cl.
*A61B 17/84* (2006.01)
*B23G 1/16* (2006.01)
*A61B 17/82* (2006.01)
*A61B 17/04* (2006.01)

(52) U.S. Cl.
CPC ................. *A61B 17/84* (2013.01); *A61B 17/82* (2013.01); *A61B 17/842* (2013.01); *B23G 1/16* (2013.01); *A61B 17/0487* (2013.01); *Y10T 408/03* (2015.01)

(58) Field of Classification Search
CPC .... A61B 17/84; A61B 17/82; A61B 17/0487; B23G 1/16

USPC .................................. 606/246–279, 300–331
See application file for complete search history.

(56) References Cited

U.S. PATENT DOCUMENTS

| | | | | |
|---|---|---|---|---|
| 5,941,669 A | * | 8/1999 | Aukzemas | 411/107 |
| 7,481,828 B2 | * | 1/2009 | Mazda et al. | 606/263 |
| 7,722,645 B2 | * | 5/2010 | Bryan | 606/246 |

FOREIGN PATENT DOCUMENTS

FR 2755843 A1 5/1998

* cited by examiner

*Primary Examiner* — Christopher Beccia
(74) *Attorney, Agent, or Firm* — Lerner, David, Littenberg, Krumholz & Mentlik, LLP

(57) ABSTRACT

A surgical assembly has a first section having a first hole with a smallest diameter and a second section having a threaded second hole with a minor thread diameter smaller than the smallest diameter of the first hole. The first hole encloses a center axis of the second hole and a clearance is provided between the first section and the second section. The assembly includes a screw member having a length for engaging the first hole and the second hole so as to bridge the clearance. The screw member has a first portion with a largest outer diameter smaller than or equal to the smallest diameter of the first hole, and a threaded second portion axially spaced from the first portion and configured to threadedly engage the second hole. A major thread diameter of the second portion is larger than the smallest diameter of the first hole.

22 Claims, 4 Drawing Sheets

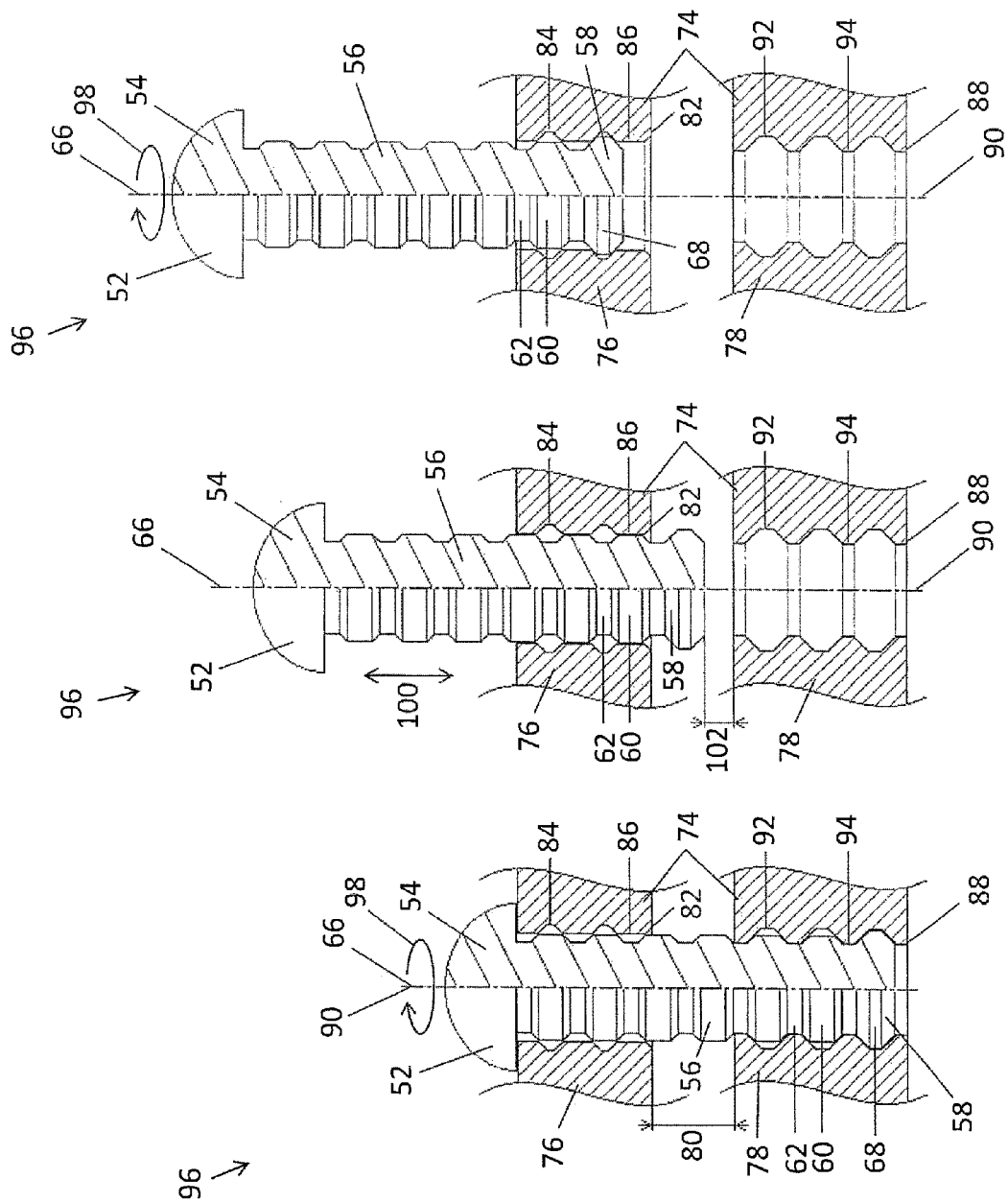

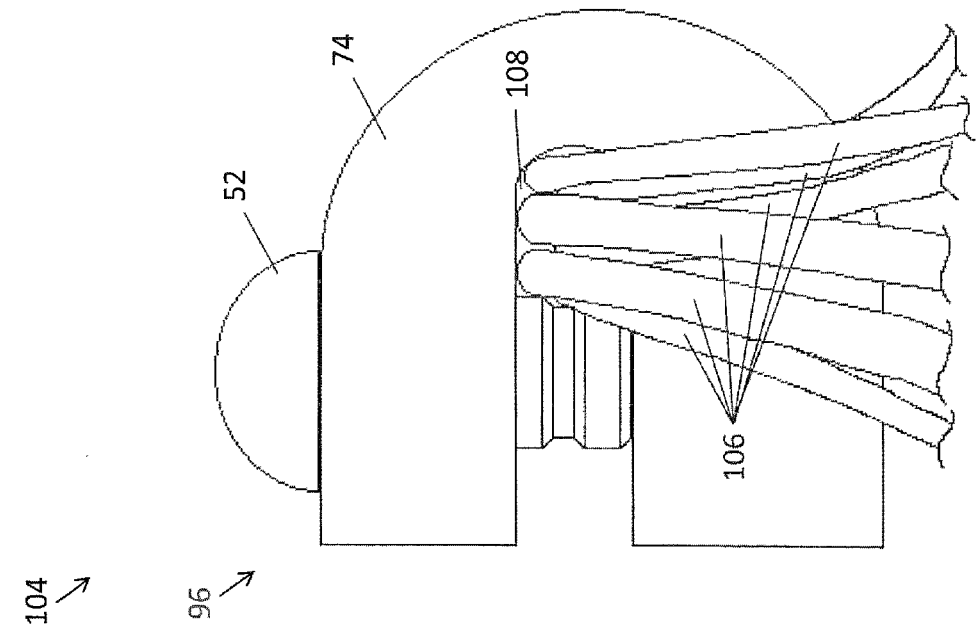
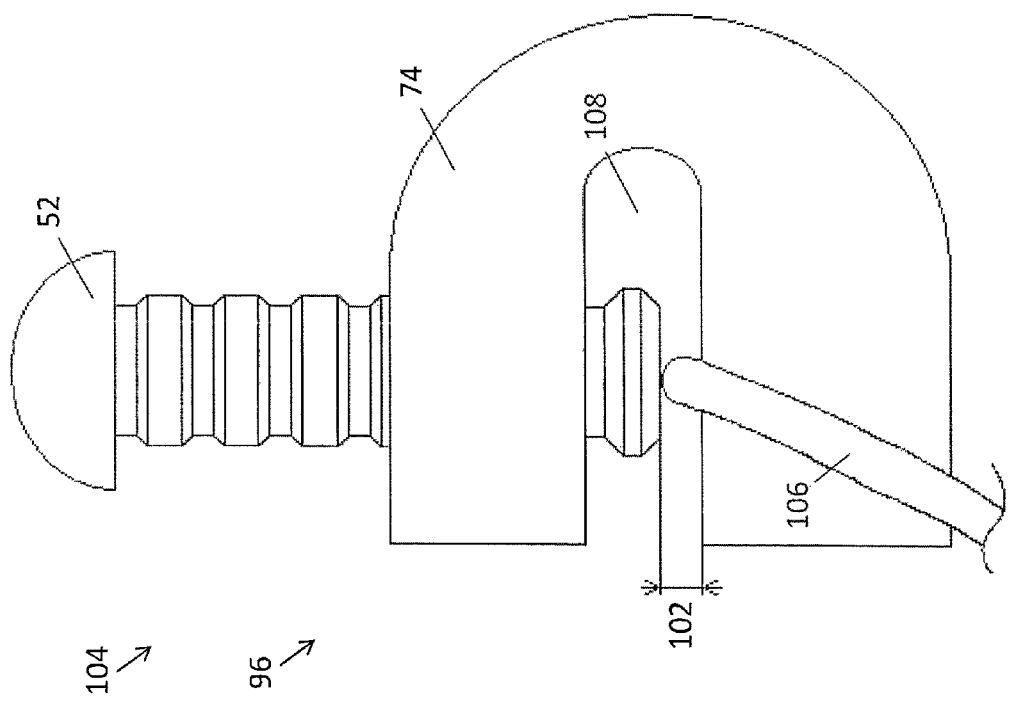
FIG. 4a
FIG. 4b

SURGICAL ASSEMBLY

CROSS-REFERENCE TO RELATED APPLICATION

The present application claims priority from European Patent Application No. 12003869.0 filed May 16, 2012, the disclosure of which is hereby incorporated herein by reference.

BACKGROUND OF THE INVENTION

The present disclosure generally relates to an assembly for use in surgical procedures. In particular, a surgical assembly and a system comprising the surgical assembly are described.

When treating a bone fracture, bone fragments are typically aligned in a first step using, for example, a bone plate. The aligned bone fragments may then be tightened together by one or more surgical cables. To prevent sections of the one or more surgical cables from interfering with, for example, surgical instruments, a surgical assembly may be used to hold together the cable sections.

A conventional surgical assembly for this purpose comprises a C-shaped clamp with two clamping arms and a screw that is to be captively held by the clamp (see also FIGS. 1a to 1c). The clamp has two coaxial threaded holes through its two arms. The screw is provided a cylindrical portion, a head at one end and a threaded portion at the other end.

In order to open the assembly for introducing cable sections, the screw needs to be unscrewed from the threaded lower hole so as to open a clearance between the two arms of the clamp. After screwing the screw again into the lower hole until its head abuts against the clamp, the clamp can be compressed by further screwing so that cable sections can be firmly held together.

The conventional assembly is bulky and requires a substantial space in the longitudinal direction of the screw. In order to overcome this drawback, the clearance of the clamp may be reduced. This in turn requires the threaded portion of the screw to be at least partly engaged with the threaded upper hole of the clamp in order for the clamping assembly to adopt the open position. As a consequence, a further drawback appears since the screw may unintentionally disengage from the assembly by movements or vibrations.

BRIEF SUMMARY OF THE INVENTION

Accordingly, there is a need for a surgical assembly which is small in size and where the screw does not easily disengage from the assembly unintentionally.

According to one aspect, a surgical assembly is provided, wherein the assembly comprises a first section having a first hole with a smallest diameter, a second section having a threaded second hole with a minor thread diameter smaller than the smallest diameter of the first hole, wherein the threaded second hole has a center axis enclosed by the first hole, a clearance between the first section and the second section, and a screw member having a length for simultaneous localization in the first hole and in the second hole so as to bridge the clearance, the screw member comprising a first portion with a largest diameter smaller than or equal to the smallest diameter of the first hole, and a threaded second portion axially spaced apart from the first portion along a longitudinal axis of the screw member and configured to threadedly engage with the threaded second hole, wherein a major thread diameter of the second portion is larger than the smallest diameter of the first hole. As used herein, major and minor thread diameters may also be referred to as major and minor threads, respectively.

The first hole may be cylindrical or conical. The second hole may be cylindrical. The first and second holes may be through holes. Alternatively, the first hole may be a through hole and the second hole may be a blind hole.

The first hole may fully enclose the screw member around its circumference. Alternatively, the first hole may only partially enclose the screw member around its circumference but still prevent the screw member from laterally disengaging from the first hole. For example, the first hole may enclose the screw member around at least 200 degrees of its circumference (e.g., 270 or more degrees).

Furthermore, the threaded second portion may be located near a distal end of the screw member. A guiding structure may be provided at the distal end of the screw member for guiding the screw member into the first and/or second hole. Such a guiding structure may have a conical appearance with a largest outer diameter smaller than a minor thread diameter of the threaded second portion.

A length of the threaded second portion along the longitudinal axis of the screw member may be smaller than the clearance. The difference in length between the clearance and the extension of the threaded second portion may be (e.g., slightly) larger than the diameter of a surgical cable, for example, the difference may be 1 to 5 mm (e.g., 3 mm). The minimum clearance may be 1.5 thread pitch of the threaded second hole. The thread of the threaded second hole may extend over slightly less than the clearance.

The first portion may be unthreaded or threaded. In a threaded implementation, the major thread diameter of the first portion may be larger than the minor thread diameter of the second hole. The handedness and, optionally, the pitch of the threads of the first portion and of the second portion may be the same. In one implementation the threaded first portion is configured to threadedly engage with the threaded second hole. A major thread diameter of the threaded first portion may be smaller than the smallest diameter of the first hole.

The first hole may be unthreaded or threaded. In a threaded implementation, the handedness and, optionally, the pitch of the threads in the first section and second section may be the same. The threaded second portion may be configured to threadedly engage with the threaded first hole. In a threaded implementation, the smallest diameter of the first hole may be defined by a minor thread diameter of the threaded first hole. In a similar manner, the largest diameter of the first portion may be defined by a major thread diameter of the first portion (when threaded). The major thread diameter of the second portion may be larger than the minor thread diameter of the first hole. The largest diameter (e.g., the major thread diameter) of the first portion may be smaller than the minor thread diameter of the first hole. As an alternative to a thread, the first hole may be provided with structures which interfere, or engage, with the major thread diameter of the second portion but not with the largest outer diameter of the first section (the major thread diameter when threaded).

When the screw member bridges the clearance, a closed void may be defined by the first section, the second section, the screw member and a structure (e.g., a sidewall) connecting the first second and the second section. The closed void may be configured to accommodate one or more surgical cables.

In general, the surgical assembly may be configured to only serve holding purposes (e.g., for a surgical cable) or to further provide a clamping function. In the latter case the surgical assembly may thus constitute a clamping assembly wherein the first section and the second section may belong (e.g., constitute integral parts of) a clamp. The clamp may generally have a C-shape.

The first and second sections may be movable relative to each other so as to vary the clearance. This movability may be realized by a section of a flexible material and/or a pivot connection between the two sections.

A pivot connection may be realized as a springingly biased hinge which allows the two sections to be compressed or pulled apart to a certain degree defined by the spring. In the case a pivot connection is implemented, the clamp may or may not be of an elastically flexible material. Moreover, the hinge may constitute an integral part of the clamp.

The screw member may comprise a head. The head may have a radial extension larger than half of the smallest diameter of the first hole. The head can thereby prevent the screw member from moving longitudinally fully through the first hole. Alternative or additional structures for preventing the screw member from moving longitudinally relative to the first section may be realized. The head may be semi-spherical, cylindrical, polygonal, a cuboid or a wing-nut. Moreover, the head may comprise notches or any other structures at its outer circumference in order to provide a better grip to the operator.

As stated above, the first section and the second section may be relatively movable (e.g., with respect to the center axis of the second hole). Due to this, the clearance can be reduced or expanded. The clearance may be reduced by threadedly engaging the threaded second portion with the threaded second hole, contacting the head with the first section and screwing the screw member. This process may be referred to as clamping. Similarly, the clearance may be expanded to an unloaded position by screwing the screw member in an opposite direction.

Regarding the relationship of the first hole and the second hole, these two holes may be coaxial. Alternatively, the features of the surgical assembly may allow a certain offset and/or inclination between a center axis of the first hole and a center axis of the second hole.

According to a further aspect, there is provided a system comprising the surgical assembly and at least one surgical cable. The clearance may be configured to accommodate the surgical cable. The surgical assembly may be configured to enclose and/or clamp the at least one surgical cable around its circumference.

According to a further aspect, there is provided a manufacturing method for the surgical assembly. The method comprises the steps of tapping a temporary hole in the first section and the second hole with a first tap in one linear relative movement, tapping the first hole by machining the circumference of the temporary hole with a second tap, and cutting a thread in at least the second hole. The method may further comprise cutting a thread in the first hole in one linear relative movement when the cutting the thread in the second hole. Alternatively, or in addition, the method may comprise the steps of threading a temporary portion and the second portion of the screw member with a die in one linear relative movement, and machining the circumference of the temporary portion into the first portion (e.g., with a cutter) in one linear relative movement.

According to a further aspect, there is provided use of the assembly for clamping at least one surgical cable.

BRIEF DESCRIPTION OF THE DRAWINGS

Further details, advantages and aspects of the present disclosure will become apparent from the following example and embodiments taken in conjunction with the drawings, wherein:

FIGS. 1a to 1c show a clamping assembly according to an example useful for understanding the embodiments, wherein FIG. 1a shows a side view of a screw member and FIGS. 1b and 1c show a cross-sectional view of a clamping assembly comprising the screw member;

FIGS. 3a to 3c show three different positions of the screw member relative to a first section and a second section of the clamp according to the embodiment; and FIGS. 4a and 4b show a system comprising two surgical cables and the surgical assembly according to the embodiment in an open and closed position, respectively.

DETAILED DESCRIPTION

Figure 1C:
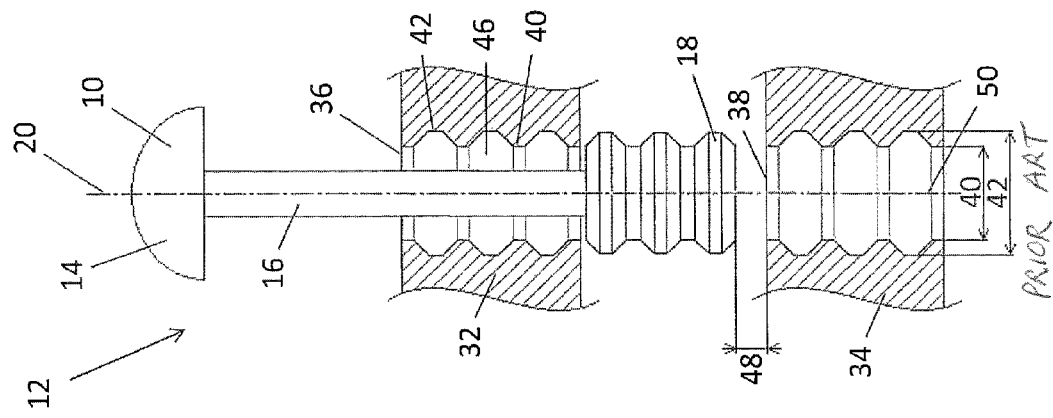

In the following, a surgical assembly and a system comprising the surgical assembly will be described. The same reference numerals will be used to denote the same or similar structural features. In the drawings the threads are only schematically shown, in particular with respect to their pitch, and do not correspond to actual realizations.

Figure 1B:
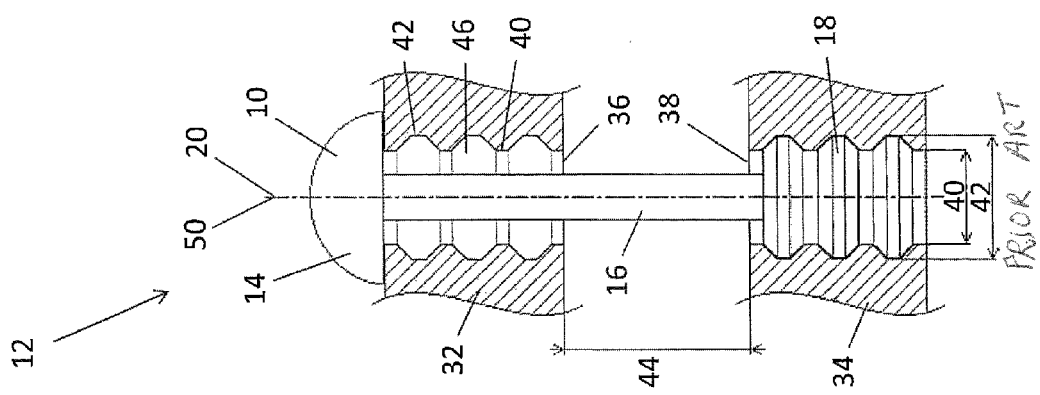
Figure 1A:
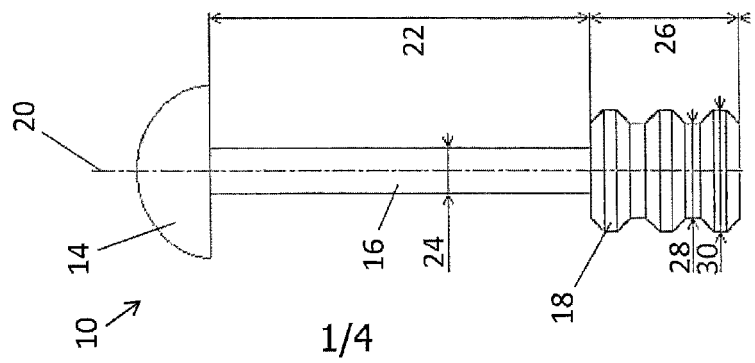

FIGS. 1a to 1c illustrate a conventional screw member 10 and a conventional clamping assembly 12 including the screw member 10. As shown in FIG. 1a, the screw member 10 comprises a head 14, a cylindrical, non-threaded first portion 16 and a cylindrical, threaded second portion 18. The length of the first portion 16 along a longitudinal axis 20 of the screw member 10 is denoted 22. The diameter of the first portion 16 is denoted 24. The second portion 18 longitudinally extends along a length 26. The threaded second portion 18 has a minor thread diameter 28 and a major thread diameter 30.

FIG. 1b shows the clamping assembly 12 in a closed position. Here, a first section 32 and a second section 34 of a C-shaped clamp can be seen (the entirety of the clamp cannot be seen in FIG. 1a or 1b). The first section 32 and the second section 34 each comprises a threaded hole 36, 38 each having a minor thread diameter 40 and a major thread diameter 42. The two threaded holes 36, 38 are coaxial and their threads are identical and correspond to the threads 28, 30 of the screw member 10. Consequently, the screw member 10 is adapted to be threadedly engaged with the upper threaded hole 36 as well as with the lower threaded hole 38.

A clearance 44 is established between the first section 32 and the second section 34. The clearance 44 is somewhat larger than the length 26 of the second portion 18.

In the situation illustrated in FIG. 1b, the screw member 10 has been screwed down through the threaded upper hole 36 and screwed into the threaded lower hole 38 until the head 14 longitudinally abuts against a top surface of the first section 32. Due to the fact that the diameter 24 of the first portion 16 of the screw member 10 is smaller than the minor thread diameter 40 of the threaded upper hole 36, a clearance 46 is established between the first portion 16 of the screw member 10 and the minor thread diameter 40 of the threaded upper hole 36.

FIG. 1c shows the clamping assembly 12 in an open position. As can be seen, the second portion 18 has been disengaged from the threaded lower hole 38. The screw member is captively held between the first section 32 and the second section 34. A clearance 48 is established between the lower end of the second portion 18 and a top surface of the second section 34. In the illustrated situation, one or more surgical cables may be introduced through this clearance 48. The surgical cables can then be enclosed by the clamping assembly 12 by screwing the screw member 10 back into the threaded lower hole 38 to the closed position as previously described and illustrated in FIG. 1b. Furthermore, a clamping force can be generated if desired by screwing the screw member to an extent that the first section 32 and the second section 34 are moved together, wherein the clearance 44 becomes smaller.

The above described clamping assembly is bulky and requires a substantial space in a longitudinal direction 50 of the threaded holes 36, 38. In order to overcome this drawback, the nominal clearance 44 may be reduced. This in turn requires the second portion 18 to be at least partly engaged with the threaded upper hole 36 in order for the clamping assembly 12 to adopt the open position. As a consequence, a further drawback appears since the screw member 10 may then unintentionally disengage from the clamping assembly 12 by movements and/or vibrations of the clamping assembly 12.

Figure 2B:
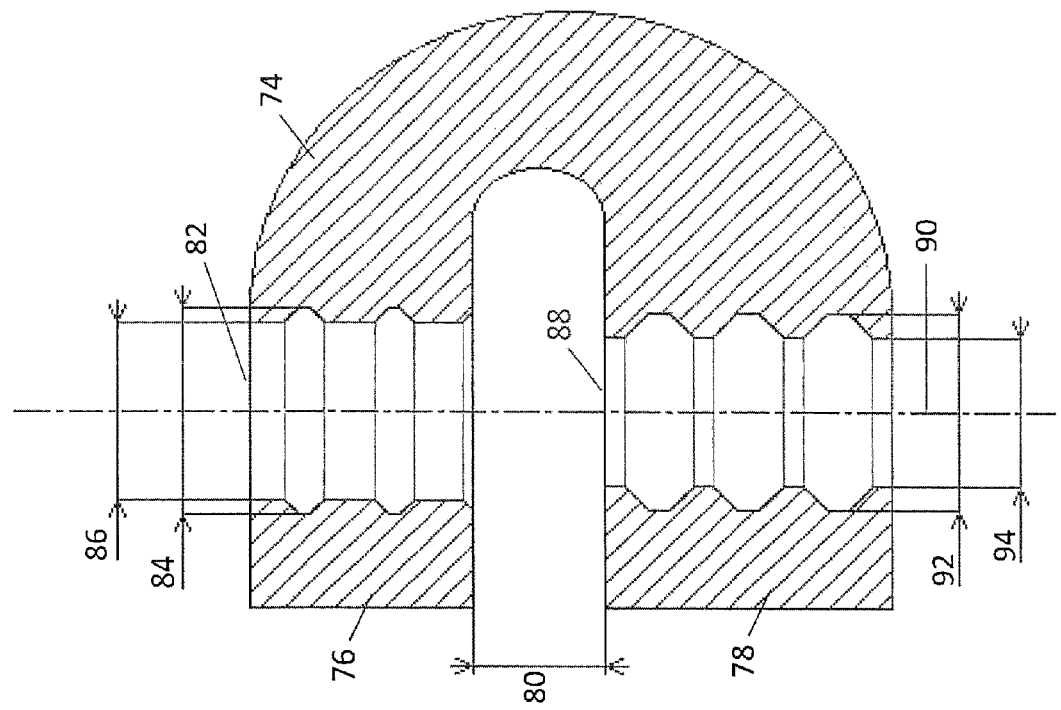
FIG. 2b shows a cross-sectional view of a clamp according to an embodiment.
Figure 2A:
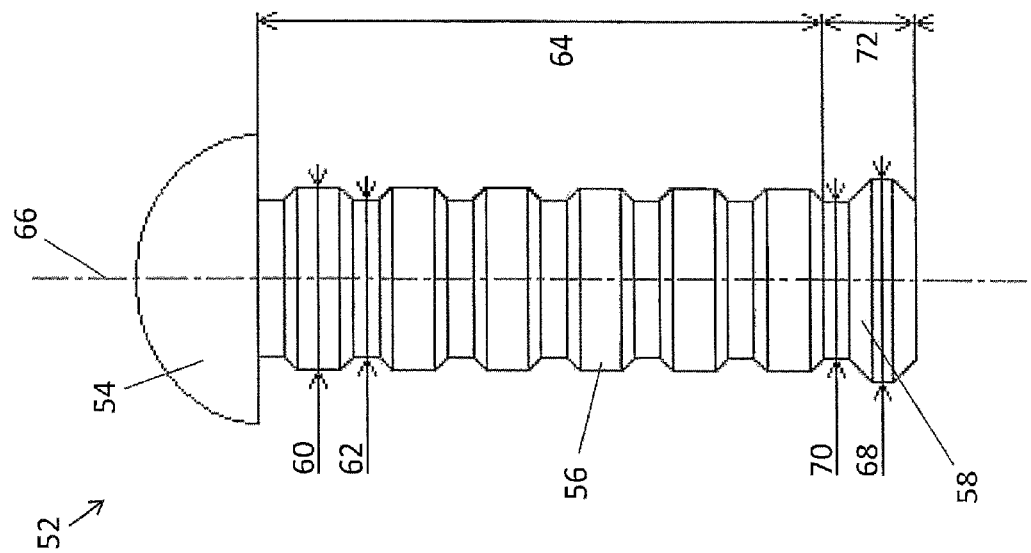
FIG. 2a shows a side view of a screw member according to an embodiment.

FIG. 2a shows a schematic side view of a screw member 52 according to an embodiment. The screw member 52 comprises a head 54 at its top end, a first portion 56 connected to the head 54 and a threaded second portion 58 at the lower distal end of the screw member 52. In the present embodiments, the first portion 56 is threaded also and has a major thread diameter 60 and a minor thread diameter 62. Furthermore, the first portion 56 extends along a distance 64 in a longitudinal direction 66 of the screw member 52, wherein the second portion 58 is axially spaced apart from the first portion 56 along this longitudinal axis 66. The second portion 58 has a major thread diameter 68 and a minor thread diameter 70 and extends along a length 72 in the longitudinal direction 66 which may correspond to 1.3 or more thread pitches. The major thread diameter 68 of the second portion 58 is larger than the major thread diameter 60 of the first portion 56.

FIG. 2b shows a cross-sectional view of an embodiment of a C-shaped clamp 74 made from a material with elastic properties. A first section 76 and a second section 78 (connected by a flexible side wall of the C that acts as a hinge) constitute integral but opposite parts of the clamp 74. Between the first section 76 and the second section 78, a clearance 80 is established. A first hole 82 is arranged through the first section 76. In this embodiment, the first hole 82 is a threaded throughhole comprising a major thread diameter 84 and a minor thread diameter 86.

Through the second section 78, a threaded second hole 88 is arranged. In this embodiment, the second hole 88 is concentric with the first hole 82. As a result, a center axis of the first hole 82 coincides with a center axis 90 of the second hole 88. The first hole 82 thereby also encloses the center axis 90 of the second hole 88. The second hole 88 comprises a major thread diameter 92 and a minor thread diameter 94. The major thread diameter 92 of the second hole 88 is equal to the major thread diameter 84 of the first hole 82. However, the minor thread diameter 94 of the second hole 88 is smaller than the minor thread diameter 86 of the first hole 82. The threads of the first hole 82 and the second hole 88 have the same pitch. The threads of the first portion 56 and the second portion 58 of the screw member 52 likewise have the same pitch (which corresponds to the pitch of the threads of the first hole 82 and a second hole 88).

FIGS. 3a to 3c show an embodiment of a surgical assembly 96 comprising the screw member 52 and the clamp 74 in three different relative positions between the screw member 52 and the clamp 74. In these figures, only a limited cross-sectional area of the clamp 74 is illustrated. The screw member 52 is in turn illustrated with a schematic side view on the left hand side and a cross-sectional view on the right hand side.

FIG. 3a illustrates a closed position of the surgical assembly 96. From the FIG. 3 it can be seen that both the major thread diameter 68 of the second portion 58 and the major thread diameter 60 of the first portion 56 of the screw member 52 are larger than the minor thread diameter 94 of the second section 78. The screw member 52 is threadedly engaged with the threaded second hole 88 by both its threaded second portion 58 and by a part of its threaded first portion 56. Due to this engagement, the screw member 52 can be longitudinally displaced relative to the clamp 74 by rotation in a direction indicated by arrow 98.

Referring to the first section 76 in FIG. 3a, it can further be seen that the major thread diameter 60 of the first portion 56 is freely smaller than the smallest diameter of the first hole 82. In this case, the major thread diameter 60 of the first portion 56 is smaller than the minor thread diameter 86 of the first hole 82. The screw member 52 has here been screwed in the second hole 88 until the head 54 abuts in the longitudinal direction 66 against an upper surface of the first section 76. By screwing the screw member 52 further, the first section 76 and the second section 78 can be pulled closer to each other, thereby reducing the clearance 80.

Referring to FIG. 3b, an open position of the surgical assembly 96 is shown. In this illustrated position, the screw member 52 is freely slidable in the longitudinal direction 66, as indicated by arrow 100, without needing to be rotated. The slideability is a result of the fact that the major thread diameter 60 of the first portion is smaller than the minor thread diameter 86 of the first hole 82.

The screw member 52 is captively held and slidable between an upper position where the second portion 58 abuts against a lower surface of the first section 76 and a lower position where the second portion 58 abuts against an upper surface of the second section 78. The position of the screw member 52 in FIG. 3b is somewhat in between the upper and lower position. As can be seen, a clearance 102 is established between the lower end of the second portion 58 of the screw member 52 and the upper surface of the second section 78. The maximum clearance 102 is accomplished when the screw member 52 is in its upper position. The clearance 102 can then be expressed as the length of the clearance 80 minus the length 72 of the second portion 58 (see FIGS. 2a and 2b).

In the illustrated open position of FIG. 3b, it is highly unlikely that the threaded second portion 58 would unintentionally engage with any of the threaded holes 82, 88. The captively held screw member 52 is therefore prevented from unintentional disengagement from the surgical assembly 96 by vibrations and/or movements of the same.

FIG. 3c illustrates disengagement of the surgical assembly 96. As can be seen, the threaded second portion 58 is threadedly engaged with the threaded first hole 82. Again, the threaded first portion 56 is not engaged with the threaded first hole 82. From this illustrated position, the screw member 52 can be disengaged from the clamp 74 (or screwed into the open position as illustrated in FIG. 3b) by rotation in the direction of the arrow 98.

FIGS. 4a and 4b show a system 104 comprising the surgical assembly 96 according to the embodiment and one or more surgical cables 106. FIG. 4a illustrates the surgical assembly 96 in the open position (see also FIG. 3b). Here, a surgical cable 106 can be introduced through the clearance 102 into a void 108. The void can be closed by bringing the screw member 52 in the position illustrated in FIG. 4b.

FIG. 4b illustrates the surgical assembly 96 in the closed position (see also FIG. 3a). As can be seen in the figure, the surgical cables 106 are enclosed in the void 108 108 defined by the screw member 52 and the clamp 74.

During surgery, when a surgeon intends to keep together a plurality of surgical cables 106, these cables 106 can be introduced through the clearance 102 of the surgical assembly 96 and accommodated in the void 108. The surgeon may then screw the screw member 52 in the position illustrated in FIG. 4b in order to close the surgical assembly 96 and thereby enclose (and, if necessary, clamp) the surgical cables 106 held in the void 108. When the surgeon later on opens the surgical assembly 96 by unscrewing the screw member 52 into the open position, the surgical cables 106 can be removed and the surgeon does not need to worry about the screw member 52 disengaging from the clamp 74.

Due to the fact that the major thread diameter 60 of the first portion 56 of the screw member 52 interacts with the second hole 88 but not with the first hole 82, the surgical assembly 96 may be made smaller in size. This is because the clearance 80 of the clamp 74 needs only be larger than the length 72 of the second portion 58 of the screw member 52.

The surgical assembly 96 can be manufactured quite easily. As for the clamp 74, with a first tap by a drill in one linear relative movement, a temporary "first" hole may be tapped in the first section 26 when also tapping the second hole 88. Then, with a second tap, the first hole 82 may be tapped by machining the circumference of the temporary "first" hole. For the second tap, a drill with a larger diameter compared to the first tap may be used. In a second step, a thread is cut in at least the second hole 88. Advantageously, in one linear relative movement (and using a single thread cutting tool) a thread may be cut in the first hole 82 and in the second hole 88.

As for the screw member 52, in one step a thread cutting tool may be used to cut a thread over the full length of a shaft of the screw member 52. In a second step, a machine operation may be applied to reduce the major thread diameter in the region of the first portion 56. These two steps may be performed in any order.

While the present disclosure has been described with reference to an exemplary embodiment, it will be appreciated that the present invention is not limited to what has been described above. For example, it will be appreciated that the dimensions of the parts may be varied as needed. Accordingly, it is intended that the present invention may be limited only by the scope of the claims appended hereto.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A surgical assembly comprising:
a first section having a first hole with a smallest diameter;
a second section having a threaded second hole with a minor thread diameter smaller than the smallest diameter of the first hole, wherein the threaded second hole has a center axis enclosed by the first hole;
a clearance between the first section and the second section; and
a screw member having a length for simultaneous localization in the first hole and in the second hole so as to bridge the clearance, the screw member comprising:
a first portion with a largest diameter smaller than or equal to the smallest diameter of the first hole; and
a threaded second portion axially spaced apart from the first portion along a longitudinal axis of the screw member and configured to threadedly engage with the threaded second hole, wherein a major thread diameter of the threaded second portion is larger than the smallest diameter of the first hole.

2. The assembly according to claim 1, wherein a length of the threaded second portion along the longitudinal axis of the screw member is smaller than the clearance.

3. The assembly according to claim 1, wherein the first portion is threaded.

4. The assembly of claim 3, wherein the threaded first portion is configured to threadedly engage with the threaded second hole.

5. The assembly of claim 3, wherein a major thread diameter of the threaded first portion is smaller than the smallest diameter of the first hole.

6. The assembly according to claim 1, wherein the first hole is threaded.

7. The assembly according to claim 6, wherein the threaded second portion is configured to threadedly engage with the threaded first hole.

8. The assembly according to claim 6, wherein the smallest diameter is defined by a minor thread diameter of the threaded first hole.

9. The assembly according to claim 6, wherein the largest diameter of the first portion is smaller than a minor thread diameter of the threaded first hole.

10. The assembly according to claim 1, wherein, when the screw member bridges the clearance, a closed void is defined by the first section, the second section, the screw member and a structure connecting the first section and the second section.

11. The assembly according to claim 1, wherein the first section and the second section constitute parts of a clamp.

12. The assembly according to claim 1, wherein the first section and the second section are relatively movable so as to vary the clearance.

13. The assembly according to claim 1, wherein the screw member comprises a head.

14. The assembly according to claim 12, wherein the clearance is configured to be reduced by threadedly engaging the threaded second portion with the threaded second hole, contacting the head with the first section and screwing the screw member.

15. The assembly according to claim 1, wherein the first hole and the second hole are coaxial.

16. A system comprising the assembly according to claim 1 and at least one surgical cable.

17. A method for manufacturing the assembly according to claim 1, comprising the steps:
tapping a temporary hole in the first section and the second hole with a first tap in one linear relative movement;
tapping the first hole by machining the circumference of the temporary hole with a second tap; and
cutting a thread in at least the second hole.

18. The method of claim 17, further comprising cutting a thread in the first hole in one linear relative movement when cutting the thread in the second hole.

19. A surgical assembly comprising:
a u-shaped clamp having a first section and a second section spaced from the first section forming a clearance therebetween, the first and second sections each having an axially aligned threaded bore therethrough, a smallest diameter of the threaded bore of the first section larger than a smallest diameter of the threaded bore of the second section; and a screw capable of simultaneously engaging the first and second clamp section threaded bores and spanning the clearance, the screw having a head, a first portion adjacent the head having a thread with a largest diameter smaller than the smallest diameter of the threaded bore in the first section and a second threaded portion spaced further from the head for engaging the threaded bore in the second clamp section, wherein a largest thread diameter in the screw second threaded portion is larger than the smallest diameter of the threaded bore in the first clamp section and less than a largest diameter of the threaded bore of the first clamp section.

20. The assembly according to claim 19, wherein a length of the threaded second portion along the longitudinal axis of the screw member is smaller than the clearance.

21. A method for manufacturing a surgical assembly comprising:
   obtaining a clamp assembly comprising a first section having a first hole with a smallest diameter, and a second section having a second hole with a diameter smaller than the smallest diameter of the first hole, wherein the second hole has a center axis enclosed by the first hole, a clearance between the first section and the second section, wherein the clamp assembly receives a screw member having a length for simultaneous localization in the first hole and in the second hole so as to bridge the clearance, the screw member having a first portion with a largest diameter smaller than or equal to the smallest diameter of the first hole, a threaded second portion axially spaced apart from the first portion along a longitudinal axis of the screw member and configured to threadedly engage with the threaded second hole, wherein a major thread diameter of the threaded second portion of the screw member is larger than the smallest diameter of the first hole;
   tapping a temporary hole in the first section and the second hole with a first tap in one linear relative movement;
   tapping the first hole by machining the circumference of the temporary hole with a second tap; and
   cutting a thread in at least the second hole.

22. The method of claim 21, further comprising cutting a thread in the first hole in one linear relative movement when cutting the thread in the second hole.

* * * * *